United States Patent [19]

Motegi et al.

[11] Patent Number: 4,978,523
[45] Date of Patent: Dec. 18, 1990

[54] MELANIN INHIBITOR

[75] Inventors: Itsuro Motegi; Michio Kawai, both of Ichikaimachi; Genji Imokawa, Utsunomiya; Koichi Nakamura, Tochigi; Naotake Takaishi, Utsunomiya, all of Japan

[73] Assignee: Kao Corporation, Tokyo, Japan

[21] Appl. No.: 814,172

[22] Filed: Dec. 24, 1985

Related U.S. Application Data

[63] Continuation of Ser. No. 601,585, Apr. 18, 1984, abandoned.

[30] Foreign Application Priority Data

Apr. 25, 1983 [JP] Japan ................................. 58-71501
Mar. 12, 1984 [JP] Japan ................................. 59-46849

[51] Int. Cl.$^5$ .......................... A61K 7/42; A61K 7/44
[52] U.S. Cl. ........................................ 424/59; 424/62; 424/DIG. 13; 424/60; 514/622; 564/170
[58] Field of Search ................... 424/59, 60, DIG. 13, 424/62; 514/622; 564/170

[56] References Cited

U.S. PATENT DOCUMENTS 3,256,312 6/1966 Strobel ................................. 424/59

OTHER PUBLICATIONS

Harry's Cosmeticology, p. 224, 7th ed., 1982.
Harry's Cosmeticology, pp. 232, 222–223.
Thoemel et al., Chem. Abstracts, vol. 96: 187112k, 1982.
Thoemel et al., Chem. Abstracts, vol. 97: 11641p.
DePolo et al., Chem. Abstracts, vol. 83: 120666g, 1975.
Thoemel et al., "Use of Etherified p-Hydroxycinnamic Acid . . ." in Chem. Abstracts, vol. 96: 187112k, 1982.
Thoemel et al., "Polyoxyalkylene Esters of Cinnamic Acid . . ." in Chem. Abstracts, vol. 97: 11641p, 1982.
De Polo et al., "Ultraviolet Light Absorber" cited in Chem. Abstracts, vol. 83: 120666g, 1975.
The Merck Index, 1976, p. 1834, Item 1832.
Hackh's Chemical Dictionary, 1969, pp. 146, 246, 288, 389, 486 and 603.

Primary Examiner—Jacqueline Stone
Attorney, Agent, or Firm—Oblon, Spivak, McClelland, Maier & Neustadt

[57] ABSTRACT

A melanin inhibitor comprising as the reactive component a cinnamic acid derivative of the formula (I) or (II):

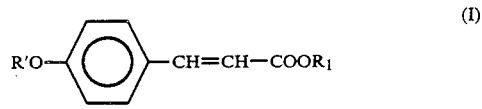

(I)

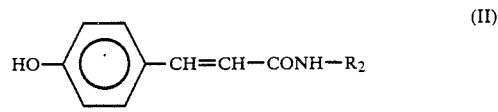

(II)

in which R' represents an acyl group having 2 to 6 carbon atoms, $R_1$ represents a hydrogen atom, an alkyl group having 1 to 6 carbon atoms, a cycloalkyl group or an alkenyl group, and $R_2$ represents a hydrogen atom, an alkyl group having 1 to 24 carbon atoms, a cycloalkyl group or an alkenyl group.

The melanin inhibitors according to the invention are locally applied to affected portions such as of freckles and pigmentary deposits after sunburn without giving any stimulative or allergic troubles to the skin.

3 Claims, No Drawings

MELANIN INHIBITOR

This application is a continuation of application Ser. No. 601,585, filed Apr. 18, 1984, now abandoned.

BACKGROUND OF THE INVENTION (i) Field of the Invention

This invention relates to melanin inhibitors and more particularly melanin inhibitors comprising a specific type of a cinnamic acid derivative as the effective component thereof.

(ii) Description of the Prior Art

Freckles, chloasma and pigmentary deposits after sunburn tend to occur or increase or become difficult to disappear with increasing age, thus being one of serious problems on skin care to persons of the middle or advanced age. The critical mechanism of these pigmentations is not known at present but it is considered that melanogenesis of melanocyte is facilitated by the action of ultraviolet rays and melanocyte-stimulating hormones. Moreover, it is considered that the tendency toward the retardation of keratinization of keratinocytes cells accompanied by the increase of age will retard the discharge of melanin to outside of the epidermis, thus developing, along with the acceleration of melanogenesis, symptoms of increasing the density of melanin granules in the epidermis or clinically increasing the pigmentary deposits.

Now, there is a high demand of medicines which act to restore acquired deposit of a pigment i.e. melanin to the normal skin color. A number of medicines have been up to now developed and put into practice. For instance, peroxides are believed to bleach melanin and thus attempts have been made in the use of hydrogen peroxide, zinc peroxide, sodium peroxide, benzoyl peroxide and the like. However, these peroxides are unstable compounds and little effects of reducing the pigmentation were not observed in practical application conditions. In recent years, cosmetics which comprise vitamin C (L-ascorbic acid) having good reducing ability were proposed, however, it showed little effects in external applications. Moreover, vitamin C is rather unstable and have disadvantage to be comprised in cosmetics.

On the other hand, in Europe and the United States of America, hydroquinone and derivatives thereof, various catechols have been used for treatment of moth patches or bleaching of colored man's skin. However, these compounds have safety problems (such as high stimulative, allergic troubles and the like) and may sometimes cause white spots, thus compounding of these substances as the medicine being rather disadvantageous. Use of a variety of melanin inhibitors has been also reported but almost all the substances showed little melanin inhibiting effects.

SUMMARY OF THE INVENTION

In view of the above, we made intensive studies through long-term investigations on the mechanism of melagenesis to find substances which are able to reduce or completely remove pigmentary deposits. As a results, it was found that cinnamic acid derivatives of a specific type have the melanin-inhibiting action and involve little or no stimulative and allergic troubles.

Accordingly, an object of the invention is to provide a melanin inhibitor which comprises an effective amount of a cinnamic acid derivative of the general formula (I) or (II)

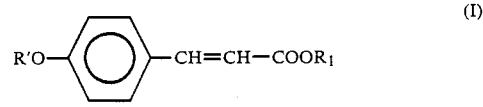

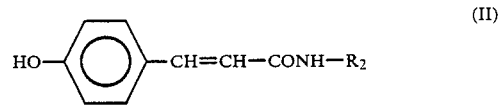

in which R' represents an acyl group having 2 to 6 carbon atoms, $R_1$ represents a hydrogen atom, an alkyl group having 1 to 6 carbon atoms, a cycloalkyl group or an alkenyl group, and $R_2$ represents a hydrogen atom, an alkyl group having 1 to 24 carbon atoms, a cycloalkyl group or an alkenyl group.

DETAILED DESCRIPTION OF THE INVENTION AND PREFERRED EMBODIMENTS

The cinnamic acid derivatives of the formula (I) used in the present invention are preferably those of the formula in which R' represents an acyl group having 2 to 6 carbon atoms, $R_1$ represents an alkyl group having 1 to 6 carbon atoms, a cycloalkyl group or an alkylene group. Preferable examples include methyl p-acetoxycinnamate, ethyl p-acetoxycinnamate, n-propyl p-acetoxycinnamate, i-propyl p-acetoxycinnamate, cyclohexyl p-acetoxycinnamate, methyl p-propionyloxycinnamate, ethyl p-propionyloxycinnamate, n-propyl p-propionyloxycinnamate, iso-propyl p-propionyloxycinnamate, cyclohexyl p-propionyloxycinnamate, methyl p-butyryloxycinnamate, ethyl p-butyryloxycinnamate, methyl p-valeryloxycinnamate, methyl p-hexanoyloxycinnamate, p-acetyloxycinnamic acid, p-propionyloxycinnamic acid, p-isopropionyloxycinnamic acid, p-butyryloxycinnamic acid, p-isobutyryloxycinnamic acid, p-valeryloxycinnamic acid, p-hexanoyloxycinnamic acid and the like.

The cinnamic acid derivatives of the formula (II) are those of the formula in which $R_2$ represents hydrogen, methyl, ethyl, n-propyl, i-propyl, n-butyl, i-butyl, sec-butyl, n-pentyl, i-pentyl, sec-pentyl, cyclopentyl, n-hexyl, cyclohexyl, heptyl, octyl, 2-ethylhexyl, capryl, lauryl, myristyl, palmityl, stearyl, isostearyl, behenyl, lignoceryl, 2-propenyl, isobutenyl, 3-pentenyl, 2-hexenyl, caproleyl, linderyl, myristoleyl, palmitoleyl, oleyl, gadoleyl, erucyl, selacholeyl and the like.

The physico-chemical properties of typical compound of the formula (II) are as follows.

TABLE 1

Physical Data of Compound (II)

| $R_2$ | m.p. (°C.) | IR (Nujol) (cm$^{-1}$) | | | Anal. Calcd for | Elemental Analysis (%) | | | |
| | | (O—H) | (N—H) | (C=O) | C H O N | Calcd Found C | H | N |
|---|---|---|---|---|---|---|---|---|
| Me | 197.3 | 3060(b) | 3460 | 1650 | 10 11 2 1 | 67.78 | 6.26 | 7.90 |

TABLE 1-continued

Physical Data of Compound (II)

| $R_2$ | m.p. (°C.) | IR (Nujol) (cm$^{-1}$) (O—H) | (N—H) | (C=O) | Anal. Calcd for C | H | O | N | Elemental Analysis (%) Calcd Found C | H | N |
|---|---|---|---|---|---|---|---|---|---|---|---|
| Et | 165.6 | 3050(b) | 3350 | 1645 | 11 | 13 | 2 | 1 | 67.79 69.09 69.35 | 6.55 6.85 6.57 | 8.02 7.33 7.29 |
| n-Pr | 142.7 | 3100(b) | 3380 | 1650 | 12 | 15 | 2 | 1 | 70.22 70.24 | 7.37 7.29 | 6.82 6.74 |
| n-Hexyl | 98.6 | 3200(b) | — | 1640 | 15 | 21 | 2 | 1 | 72.84 72.88 | 8.56 8.43 | 5.66 5.60 |
| cyclo-Hexyl | 209.5 (dec.) | 3000(b) | 3380 | 1645 | 15 | 19 | 2 | 1 | 73.44 73.44 | 7.81 7.69 | 5.71 6.00 |

(b)broad

TABLE 2

The H-NMR and UV data of Compound (II)

| $R_2$ in Formula (II) | H-NMR (CD$_3$OD) δ ppm from TMS $R_2$ | C=C—H$^a$ | Ar—H | UV (EtOH) λ max (nm) | logε |
|---|---|---|---|---|---|
| Me | 2.80(3H,s) | 6.36(1H,d) 7.46(1H,d) | 6.7–7.6(4H,m) | 292 308 | 4.34 4.32 |
| Et | 1.17(3H,t,J = 8.0 Hz) 3.30(2H,q,J = 8.0 Hz) | 6.35(1H,d) 7.46(1H,d) | 6.6–7.6(4H,m) | 292 308 | 4.37 4.36 |
| n-Pr | 0.92(3H,t,J = 6.0 Hz) 1.53(2H,q,t,J = 6.0,7.0 Hz) 3.26(2H,t,J = 7.0 Hz) | 6.25(1H,d) 7.41(1H,d) | 6.6–7.5(4H,m) | 292 308 | 4.41 4.40 |
| n-Hexyl | 0.88(3H,t,J = 5.2 Hz) 0.8–1.9(8H,m) 3.27(2H,t,J = 7.0 Hz) | 6.38(1H,d) 7.47(1H,d) | 6.6–7.6(4H,m) | 293 308 | 4.37 4.36 |
| cyclo-Hexyl (DMSO) | 0.5–2.2(10H,m) 3.1–4.2(1H,m) | 6.42(1H,d) 7.63(1H,d) | 6.5–7.6(4H,m) | 293 310 | 4.40 4.39 |

$^a$The coupling constant between the two adjacent vinyl protons (J = 16.0 Hz) indicates that these protons are in trans positions with each other.

The cinnamic acid derivatives of the invention are known per se or may be prepared by any known techniques. For instance, the compounds of the formula (I) are prepared according to the following reaction formulas which comprise subjecting p-hydroxycinnamic acid and an alcohol to esterification reaction in the presence of an acid catalyst (sulfuric acid, p-toluenesulfonic acid or the like) to give a p-hydroxycinnamic acid ester, and acylating the ester by any known manner.

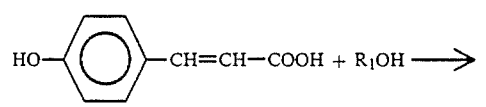

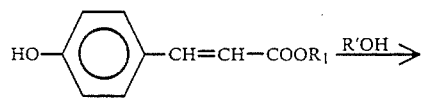

in which R' and $R_1$ have the same meanings as defined before, respectively. The intermediate p-hydroxycinnamic acid ester may be prepared by subjecting p-hydroxybenzaldehyde and malonic acid monoester to condensation reaction.

The compounds of the formula (II) may be prepared, for example, according to the following reaction sequence.

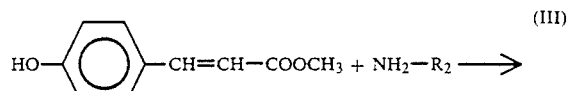
(III)

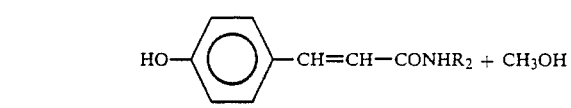
(II)

CH$_3$COO—⟨◯⟩—CH=CH—COCl + 3R$_2$NH$_2$ ⟶

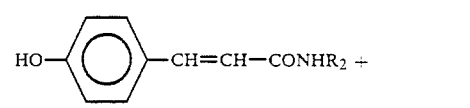

R$_2$NHOCCH$_3$ + R$_2$NH$_3$$^+$Cl$^-$ in which $R_2$ has the same meaning as defined before.

The melanin inhibitors of the invention should preferably contain 0.01 to 50 wt % (hereinafter referred to simply as %), preferably from 1 to 20%, of the cinnamic acid derivative of the formula (I) or (II).

The melanin inhibitor may take various preparation forms including lotions, emulsions, creams, ointments, sticks, solutions in organic solvents, packs, and gel. The melanin inhibitor may be admixed with any arbitrary ingredients as ordinarily used in cosmetics such as, for example, oily substances, humectants, thickeners, preservatives, emulsifiers, medical ingredients, perfumes, emulsification stabilizers and the like. The melanin-inhibiting effect may be further improved when using the cinnamic acid derivatives in combination with other ingredients such as allantoin, vitamin E acetate, glycyrrhizin, salicylic acid, urea, coix seed and various plant extracts. In addition, addition of various UV absorbers may be effective in providing melanin inhibitors having both sunburn-preventing and curing effects.

The melanin inhibitors of the invention are locally applied to affected portions such as freckles and pigmentary deposits after sunburn. With cream and ointment preparations, they are preferably applied in an amount of 1 to 20 mg per $cm^2$ of the skin. With liquid preparations, the amount ranges 1 to 10 mg per $cm^2$.

By the local application of the melanin inhibitor of the invention, the affected portion can be returned to a normal skin. This inhibitor is completely different from existing sun screens which serve to prevent sunburn.

It will be noted that the cinnamic acid derivatives of the formula (I) are more compatible with various types of carriers than other compounds such as p-hydroxycinnamic acid, thus providing melanin inhibitors which can be stably preserved on a longer term.

The present invention is described in more detail by way of test examples, examples and references.

TEST EXAMPLE 1

Effect on UV Pigmentary Spots of Guinea Pig

Laboratory animals having acquired pigmentary spots were used to determine the effect of reducing pigmentation. The results are shown in Table 1.

[Test Method]

Yellow guinea pigs, which resemble yellow people with respect to skin color and pigmentary spots were treated to Uv ray radiation. In about 4 days of UV radiation, the guinea pigs suffered melanism which was maximized in about 8 days. These guinea pigs were used as the laboratory animals. The hair on the back of each guinea pig was cut with a hair cutter and shaved with an electric shaver. The guinea pig was covered on the thus shaved back with an aluminium foil sheet having six rectangular openings with a size of 2.5×2 cm, followed by irradiation of UV-B (six SE lamps, 3.0 mW/$cm^2$) once a day for 5 minutes over three successive days. On fourteenth day after the irradiation, six pigmentary deposits were applied with a 10% ethanol solution of compound (I) twice a day over 25 successive days. The degree of melanism of the skin was visually judged according to the following assessment standard. The effect was represented by an average of evaluation points.

| Standard | Evaluation Point | |
|---|---|---|
| − | 0 | No pigmentary deposits were found. |
| ± | 1 | A slight degree of pigmentary deposits was found though the boundaries were not clear. |
| + | 2 | A moderate degree of pigmentary deposits was found with clear boundaries. |
| ++ | 3 | Intense pigmentary deposits with clear boundaries. |

[Results]

TABLE 1

| Test Compounds | | Prior to Application | After 20 Days |
|---|---|---|---|
| n-Propyl p-acetoxycinnamate | 10% | 2.8 ± 0.42 | 1.2 ± 0.52 |
| i-Propyl p-acetoxycinnamate | 10% | 2.7 ± 0.48 | 1.2 ± 0.79 |
| Cyclohexyl p-acetoxycinnamate | 10% | 2.6 ± 0.52 | 1.3 ± 0.67 |
| i-Propyl p-propionyloxycinnamate | 10% | 2.6 ± 0.52 | 1.3 ± 0.67 |
| Control (ethanol alone) | | 2.7 ± 0.48 | 2.5 ± 0.71 |

TEST EXAMPLE 2

Effect on UV Pigmentary Spots of Guinea Pig

Laboratory animals having the ability of forming acquired pigmentary spots were used and pigmentary spots were formed on the animals for determination of the improved effects. The results are shown in Table 2.

[Test Method]

Yellowish brown guinea pigs which were used as the laboratory animals because the yellow guinea pigs resembled yellow people with respect to the skin color and pigmentary spots started to be produced in about 4 days after irradiation of UV rays similar to men and the melanism became of its maximum in about 8 days were used as laboratory animals. The hair on the back of each guinea pig was cut with a hair cutter and shaved with an electric shaver. The guinea pig was covered on the thus shaved back with an aluminium foil sheet having six square openings with a size of 1.5×1.5 cm, followed by irradiation of UV-B (six SE lamps, 3.0 mW/$cm^2$) once a day for 5 minutes over three successive days. On fourteenth day after the irradiation, a 10% ethanol solution of compound (II) was applied to six pigmentary deposit site twice a day over 30 successive days. The degree of melanism of the skin was visually judged according to the following assessment standard of Test Example 1. The effect was represented by an average of evaluation points.

[Results]

TABLE 2

| Test Compounds | Prior to Application | After 30 Days |
|---|---|---|
| N-Methyl-p-hydroxycinnamamide | 2.5 ± 0.53 | 1.3 ± 0.48 |
| N-Ethyl-p-hydroxycinnamamide | 2.6 ± 0.52 | 1.5 ± 0.53 |
| N-Propyl-p-hydroxycinnamamide | 2.6 ± 0.52 | 1.6 ± 0.52 |
| N-Hexyl-p-hydroxycinnamamide | 2.4 ± 0.52 | 1.4 ± 0.52 |
| N-cyclohexyl-p-hydroxycinnamamide | 2.5 ± 0.53 | 1.7 ± 0.67 |
| Control (ethanol alone) | 2.5 ± 0.53 | 2.3 ± 0.67 |

TEST CONTROL 3

Effect on Human UV Pigmentary Spots

The effects of compounds (I) of the invention on persons was checked. A black rubber plate having three round openings with a diameter of 1 cm was attached to fifteen healthy males on the back. Thereafter, UV-B (four SE lamps, 1.2 mW/cm$^2$) was irradiated once a day for 1 to 3 minutes over 3 successive days. The MED of each person being tested was measured and the energy of the UV-B was determined to be about 1.5 MED. After the irradiation, pigmentary deposits developed. From the 14th day after the irradiation at which the pigmentary spots became darkest, a cream containing 5% of compound (I) (having a formulation indicated in Example 5) has been applied once a day in an amount of about 15 mg/80 mm$^2$. In six weeks after commencement of the application, the color of the pigmentary spots to which a cream containing compound (I) was applied was compared with control [a spot to which a cream without compound (I) was applied]. The results are shown in Table 3.

TABLE 3

| Subject No. | Prior to Application | Site Applied with Base Cream | Site Applied with Cream Containing 5% n-propyl Acetoxycinnamate |
|---|---|---|---|
| 1 | ++ | + | ± |
| 2 | ++ | + | ± |
| 3 | ++ | + | − |
| 4 | + | ± | ± |
| 5 | ++ | − | − |
| 6 | ++ | + | ± |
| 7 | ++ | + | ± |
| 8 | ++ | + | ± |
| 9 | ++ | + | ± |
| 10 | ++ | + | ± |
| 11 | + | + | − |
| 12 | ++ | ± | − |
| 13 | ++ | + | − |
| 14 | + | ± | ± |
| 15 | ++ | + | ± |
| Average | 2.8 ± 0.41 | 1.67 ± 0.62 | 0.67 ± 0.49 |

Note: The evaluation standard is the same as in Test Example 1. The sites applied with the cream of the invention showed neither stimulative nor allergic reaction.

TEST EXAMPLE 4

Effect on Human UV Pigmentary Spots

The effect of compounds (II) of the invention on persons was checked. Twenty healthy males were each covered at the flexor side of one forehand with an aluminium foil having square openings with a size of 1.5×1.5 cm, followed by irradiation of UV-B (four SE lamps, 2.1 mV) once a day for 1 to 3 minutes over three successive days. From 14th day after the irradiation at which pigmentary deposits developed and became darkest in color, an ethanol solution and a cream each containing 10% of compound (II) (having formulations of Examples 12 and 13, respectively) were each applied twice a day in an amount of 20 mg/225 mm$^2$. Four weeks after commencement of the application, the applied sites were compared with controls in which ethanol alone and a base cream (containing no compound (II)) were, respectively, applied to. The judgement was effected in the same manner as in Test Example 1. The results are shown in Table 4.

TABLE 4

| Subject No. | Prior to Application | After Application for 40 Days | | |
|---|---|---|---|---|
| | | 10% N-methyl-p-Hydroxy-cinnamamide | 10% N-propyl-p-hydroxy-cinnamamide | Ethanol |
| 1 | ++ | ± | ± | + |
| 2 | ++ | − | ± | ++ |
| 3 | ++ | ± | ± | + |
| 4 | ++ | − | − | ± |
| 5 | ++ | ± | − | + |
| 6 | + | − | − | + |
| 7 | ++ | ± | + | + |
| 8 | ++ | ± | ± | + |
| 9 | ++ | ± | ± | + |
| 10 | ++ | − | − | ++ |
| 11 | ++ | ± | ± | ++ |
| 12 | + | − | − | ± |
| 13 | ++ | − | ± | + |
| 14 | ++ | − | ± | ± |
| 15 | + | − | − | ± |
| 16 | + | − | ± | + |
| 17 | ++ | ± | ± | + |
| 18 | ++ | − | ± | + |
| 19 | ++ | − | − | ± |
| 20 | ++ | ± | ± | ± |
| Average | 2.75 ± 0.44 | 0.45 ± 0.51 | 0.70 ± 0.57 | 1.85 ± 0.67 |

TEST EXAMPLE 5

Effect on Human Pigmentary Spots (Chloasma)

Human pigmentary spots (chloasma) were applied with a cream containing 5% of compound (I) (having a formulation of Example 5) once a day in an amount of about 15 mg/80 mm$^2$ over 6 weeks. Eight weeks after the application, the intensity of the color of the pigmentary spots was judged. The results are shown in Table 5.

TABLE 5

| Subject No. | Prior to Application | After 8 Weeks |
|---|---|---|
| 1 | 3 | 2 |
| 2 | 3 | 1 |
| 3 | 2 | 1 |
| 4 | 2 | 1 |
| 5 | 3 | 1 |
| Average | 2.6 | 1.2 |

As will be clearly seen from the above results, the intensity of the color of pigmentary spots are reduced. Neither stimulative nor allergic reaction is recognized.

TEST EXAMPLE 6

Compatibility of compounds (I) of the invention with several carriers were checked. The test was effected as follows: 10 g of a compound being tested was added to 90 g of a carrier and the compatibility was judged according to the following evaluation standard. The results are shown in Table 6.

[Evaluation Standard]

O Perfectly clear
Δ Slightly clouded
X Clouded or precipitated

TABLE 6

| Carrier | Compounds of the Invention | | Comparative Compound |
|---|---|---|---|
| | Ethyl p-Acet-oxycinnamate | p-(2-ethyl) butyloxy-cinnamic acid | p-Hydroxy-cinnamic acid |
| Isopropyl myristate | O | O | X |

TABLE 6-continued

| Carrier | Compounds of the Invention | | Comparative Compound |
|---|---|---|---|
| | Ethyl p-Acet-oxycinnamate | p-(2-ethyl) butyloxy-cinnamic acid | p-Hydroxy-cinnamic acid |
| Neopentyl glycol di-2-ethylhexyl | O | O | X |
| Di-isostearyl malate | O | O | X |

EXAMPLE 1

Lotion-type Melanin Inhibitor

| (Formulation) | |
|---|---|
| n-Propyl p-acetoxycinnamate | 5.0% |
| Glycerine | 4.0% |
| Polyoxyethylene hardened castor oil | 1.5% |
| Ethanol | 10.0% |
| Sodium pyrrolidonecarboxylate | 2.0% |
| Perfume | small amount |
| Purified water | balance |
| | 100.0% |

EXAMPLE 2

Oil Essence-type Melanin Inhibitor

| (Formulation) | |
|---|---|
| Methyl p-acetoxycinnamate | 5.0% |
| Mink oil | 55.0% |
| Wheat embryo oil | 40.0% |

EXAMPLE 3

W/O-type Moisture Cream-type Melanin Inhibitor

| (Formulation) | |
|---|---|
| n-Propyl p-propionyloxycinnamate | 5.0% |
| Vaseline (Petroleum Jelly) | 6.0% |
| Cholesterol | 0.6% |
| Cetanol | 0.5% |
| Sorbitan sesqui-oleate | 2.0% |
| Liquid lanolin | 4.0% |
| Iso-propyl palmitate | 8.0% |
| Squalane | 10.0% |
| Solid paraffin | 4.0% |
| Butylparaben | 0.1% |
| Methylparaben | 0.1% |
| Glycerine | 3.0% |
| Perfume | 0.2% |
| Purifed water | balance |

EXAMPLE 4

O/W-type Moisture Cream-type Melanin Inhibitor

| (Formulation) | |
|---|---|
| n-Propyl p-acetoxycinnamate | 5.0% |
| Stearic acid | 2.0 |
| Cetanol | 4.0 |
| Vaseline (Petroleum Jelly) | 5.0 |
| Squalane | 8.0 |
| Hardened palm oil | 4.0 |
| Polyoxyethylene sorbitan monostearate (20 E.O.) | 1.4 |
| Glycerine monostearate | 2.4 |
| Butylparaben | 0.1 |
| Methylparaben | 0.1 |
| Glycerine | 3.0 |
| Dipropylene glycol | 3.0 |
| L-arginine | 10.0 |
| Potassium hydroxide | 0.2 |
| Perfume | 0.2 |
| Purified water | balance |

EXAMPLE 5

Emulsion-type Melanin Inhibitor

| (Formulation) | |
|---|---|
| Ethyl p-acetoxycinnamate | 5.0% |
| Stearic acid | 1.0 |
| Cetanol | 2.0 |
| Vaseline (Petroleum Jelly) | 2.5 |
| Squalane | 4.0 |
| Hardened palm oil | 2.0 |
| Polyoxyethylene sorbitan monostearate (20 E.O.) | 1.4 |
| Glycerine monostearate | 1.2 |
| Butylparaben | 0.1 |
| Methylparaben | 0.1 |
| Glycerine | 3.0 |
| Dipropylene glycol | 3.0 |
| Potassium hydroxide | 0.2 |
| Carboxy vinyl polymer | 0.2 |
| Perfume | 0.2 |
| Purified water | balance |

EXAMPLE 6

Pack-type (pasty peel-off type) Melanin Inhibitor

| (Formulation) | |
|---|---|
| n-Propyl p-acetoxycinnamate | 10.0 |
| Polyvinyl alcohol | 12.0 |
| Sodium carboxymethyl cellulose | 3.0 |
| Dipropylene glycol | 2.0 |
| Glycerine | 2.0 |
| Ethanol | 5.0 |
| Olive oil | 3.0 |
| Polyoxyethylene hardened castor oil (E.O. addition 30 moles) | 0.5 |
| Titanium oxide | 8.0 |
| Kaolin | 6.0 |
| Perfume | 0.1 |
| Methylparaben | 0.1 |
| Purified water | balance |

EXAMPLE 7

Ointment-type Melanin Inhibitor

| (Formulation) | |
|---|---|
| Cyclohexyl p-acetoxycinnamate | 10% |
| White vaseline | 90 |

EXAMPLE 8

Liquid-type Melanin Inhibitor

| (Formulation) | |
|---|---|
| Ethyl p-acetoxycinnamate | 10% |
| Ethanol | 90 |

EXAMPLE 9

Lotion-type Melanin Inhibitor (Formulation)

| | |
|---|---|
| N-methyl-p-hydroxycinnamamide | 5.0% |
| Glycerine | 4.0 |
| Polyoxyethylene hardened castor oil | 1.5 |
| Ethanol | 10.0 |
| Sodium pyrrolidonecarboxylate | 2.0 |
| Perfume | small amount |
| Purified water | balance |
| | 100.0% |

EXAMPLE 10

Oil Essence-type Melanin Inhibitor (Formulation)

| | |
|---|---|
| N-ethyl-p-hydroxycinnamamide | 5% |
| Mink Oil | 55 |
| Wheat embryo oil | 40 |
| | 100% |

EXAMPLE 11

Powder Essence-type Melanin Inhibitors (Formulation)

| | |
|---|---|
| N-propyl-p-hydroxycinnamamide | 5% |
| Mannitol | 95 |
| | 100% |

EXAMPLE 12

W/O-type Moisture Cream-type Melanin Inhibitor (Formulation)

| | |
|---|---|
| N-hexyl-p-hydroxycinnamamide | 5.0% |
| Vaseline (Petroleum Jelly) | 6.0 |
| Cholesterol | 0.6 |
| Cetanol | 0.5 |
| Sorbitan sesqui-oleate | 2.0 |
| Liquid lanolin | 4.0 |
| Isopropyl palmitate | 8.0 |
| Squalane | 10.0 |
| Solid paraffin | 4.0 |
| Butylparaben | 0.1 |
| Methylparaben | 0.1 |
| Glycerine | 3.0 |
| Perfume | 0.2 |
| Purified water | Balance |
| | 100.0% |

EXAMPLE 13

O/W-type Moisture Cream-type Melanin Inhibitor (Formulation)

| | |
|---|---|
| N-methyl-p-hydroxycinnamamide | 5.0% |
| Stearic acid | 2.0 |
| Cetanol | 4.0 |
| Vaseline (Petroleum Jelly) | 5.0 |
| Squalane | 8.0 |
| Hardened palm oil | 4.0 |
| Polyoxyethylene(20) sorbitan monostearate | 1.4 |
| Glycerine monostearate | 2.4 |
| Butylparaben | 0.1 |

-continued (Formulation)

| | |
|---|---|
| Methylparaben | 0.1 |
| Glycerine | 3.0 |
| Dipropylene glycol | 3.0 |
| Potassium hydroxide | 0.2 |
| Perfume | 0.2 |
| Purified water | balance |
| | 100% |

EXAMPLE 14

Emulsion-type Melanin Inhibitor (Formulation)

| | |
|---|---|
| N-cyclohexyl-p-hydroxycinnamamide | 5.0% |
| Stearic acid | 1.0 |
| Cetanol | 2.0 |
| Vaseline (Petroleum Jelly) | 2.5 |
| Squalane | 4.0 |
| Hardened palm oil | 2.0 |
| Polyoxyethylene (20) sorbitan monostearate | 1.4 |
| Glycerine monostearate | 1.2 |
| Butylparaben | 0.1 |
| Methylparaben | 0.1 |
| Glycerine | 3.0 |
| Dipropylene glycol | 3.0 |
| Potassium hydroxide | 0.2 |
| Carboxy vinyl polymer | 0.2 |
| Perfume | 0.2 |
| Purified water | Balance |
| | 100.0% |

EXAMPLE 15

Pack-type (pasty peel-off type) Melanin Inhibitor (Formulation)

| | |
|---|---|
| N-methyl-p-hydroxycinnamamide | 10.0% |
| Polyvinyl alcohol | 12.0 |
| Sodium carboxymethyl cellulose | 3.0 |
| Dipropylene glycol | 2.0 |
| Glycerine | 2.0 |
| Ethanol | 5.0 |
| Olive oil | 3.0 |
| Polyoxyethylene hardened oil (30 E.O.) | 0.5 |
| Titanium oxide | 8.0 |
| Kaolin | 6.0 |
| Perfume | 0.1 |
| Methylparaben | 0.1 |
| Purified water | Balance |
| | 100.0% |

EXAMPLE 16

Ointment-type Melanin Inhibitor (Formulation)

| | |
|---|---|
| N-Hexyl-p-hydroxycinnamamide | 10% |
| White vaseline | 90% |

EXAMPLE 17

Liquid-type Melanin Inhibitor (Formulation)

| | |
|---|---|
| N-methyl-p-hydroxycinnamamide | 10% |

-continued

| (Formulation) | |
| --- | --- |
| Ethanol | 90% |

REFERENCE 1

Preparation of n-Propyl p-acetoxycinnamate (i) 19.7 g (0.12 mole) of p-hydroxycinnamic acid was dissolved in a mixed solvent of 80 ml of n-propyl alcohol and 10 ml of ether, into which was added dropwise a solution of 25 g (0.12 mole) of dicyclohexylcarbodimide in 20 ml of ether in about 15 minutes under ice-cooling conditions. After stirring for 1 hour in ice-cooling conditions, the mixture was stirred for 5 hours at room temperature to complete the reaction. Then the reaction mixture was poured into a large amount of aqueous saturated ammonium chloride solution, to which was added 300 ml of ethyl acetate. The mixture was sufficiently stirred. The resulting crystalline N,N-dicyclohexylurea was removed by filtration, after which the solution was separated into an organic phase and an aqueous phase. The aqueous phase was extracted once with ethyl acetate. The organic phase was gathered and dried over anhydrous sodium sulfate, and the solvent was removed by distillation to give a residue. The residue was dissolved in a mixed solvent of hexane and ethyl acetate (4:1) and insoluble matters were removed by filtration. N-propyl p-hydroxycinnamate was isolated by the high speed liquid chromatography (silica gel: 30 cm, eluant: hexane/ethyl acetate=4/1). The isolated cinnamate was recrystallized from methanol for purification. Yield=87%.

Melting point: 72.5°–73° C.

| Elementary analysis: | C | H |
| --- | --- | --- |
| Calculated for $C_{12}H_{14}O_3$ | 69.89 | 6.84 |
| Found | 69.60 | 6.55 |

IR (KBr, cm$^{-1}$) 3260 (OH), 1670 (CO).

NMR (CDCl$_3$, TMS internal standard, δ): 0.98 (3H, t, J=7.5 Hz, CH$_3$—). 1.72 (2H, q, t, J=7.5 Hz, J=6.5 Hz, —CH$_2$—). 4.17 (2H, t, J=6.5 Hz, —CH$_2$—). 6.26 (d, J=16.0 Hz, C=C—H). 7.67 (d, J=16.0 Hz, C=C—H). 6.92 (2H, d-m, J-9.0 Hz, Ar-H). 7.41 (2H, d-m, J-9.0 Hz, Ar-H).

(ii) 9.7 g (0.0471 mole) of the n-propyl p-hydroxycinnamate obtained in (i) and 4.5 g (0.0565 mole) of pyridine were dissolved in 50 ml of benzen, into which was added dropwise a solution of 4.4 g (0.565 mole) of acetyl chloride in 20 ml of benzene in 15 minutes while stirring under ice-cooling conditions. The mixture was stirred for 1 hour under ice-cooling conditions and for 4 hours at room temperature, to complete the reaction. Then the reaction mixture was poured into a large amount of aqueous saturated sodium hydrogencarbonate solution and stirred for 1 hour. The mixture was extracted with ether and the ether phase was washed with 10N HCl and then with aqueous saturated sodium hydrogencarbonate solution. The thus treated ether layer was dried over anhydrous sodium sulfate and the solvent was distilled off to give a residue. The residue was separated by the high speed liquid chromatography (silica gel, eluant: hexane/ethyl acetate=5/1) to give intended n-propyl p-acetoxycinnamate in pure form. Yield: 96%.

Melting Point: 66.0°–67.0° C.

| Elementary analysis: | C | H |
| --- | --- | --- |
| Calculated for $C_{14}H_{16}O_4$ | 67.73 | 6.50 |
| Found | 68.00 | 6.76 |

IR (KBr, cm$^{-1}$): 1700 (CO), 1740 (CO).

NMR (CDCl$_3$, TMS internal standard, δ): 0.98 (3H, t, J=7.0 Hz, CH$_3$—). 1.72 (2H, q, t, J=7.0 Hz, J=6.5 Hz, —CH$_2$—). 2.27 (3H, s. CH$_3$CO). 4.17 (2H, t, J=6.5 Hz, —CH$_2$—). 6.40 (1H, C=C-H). 7.71 (1H, C=C-H). 7.12 (2H, Ar-H). 7.56 (2H, Ar-H).

REFERENCE 2

Preparation of i-Propyl p-propionyloxycinnamate (i) The procedure of Reference 1 (i) was repeated using i-propyl alcohol instead of n-propyl alcohol thereby obtaining i-propyl p-hydroxycinnamate. Yield: 92%.

Melting point 70°–71° C.

| Elementary analysis: | C | H |
| --- | --- | --- |
| Calculated for $C_{12}H_{14}O_3$ | 69.89 | 6.84 |
| Found | 70.16 | 7.01 |

IR (KBr, cm$^{-1}$): 3375 (OH), 1670 (CO).

NMR (CDCl$_3$, TMS internal standard, δ): 1.33 (6H, d, J=6.5 Hz, CH$_3$—). 5.17 (1H, sep, J=6.5 Hz, $$-CH\diagup_{\diagdown}),$$

6.17 (1H, d, J=16.0 Hz, C=C-H), 7.68 (1H, d, J=16.0 Hz, C=C-H), 6.90 (2H, d-m, J=9.0 Hz, Ar-H), 7.42 (2H, d-m, J=9.0 Hz, Ar-H).

(ii) 9.7 g (0.0471 mole) of the i-propyl p-hydroxycinnamate obtained in (i) was allowed to be reacted with 5.2 g (0.0565 mole) of propyonyl chloride in the same manner as in (ii) of Reference 1, thereby obtaining i-propyl p-propionyloxycinnamate. Yield: 95%.

Melting point: 33.5°–34.0° C.

| Elementary analysis: | C | H |
| --- | --- | --- |
| Calculated for $C_{15}H_{18}O_4$ | 68.69 | 6.92 |
| Found | 68.65 | 6.98 |

IR (KBr, cm$^{-1}$): 1705 (CO), 1755 (CO).

NMR (CDCl$_3$, TMS internal standard, δ): 1.24 (3H, t, J=7.0 Hz, CH$_3$CH$_2$—) 1.32 (6H, d, J=6.5 Hz, CH$_3$CH—)CH$_2$ 2.58 (2H, q, J=7.0 Hz, CH$_3$CH$_2$—) 5.35 (1H, sep, J=6.5 Hz, $$-CH\diagup_{\diagdown}),$$

6.37 (1H, C=C-H), 7.70 (1H, C=C-H), 7.13 (2H, Ar-H), 7.56 (2H, Ar-H).

Reference 3

The general procedure of References 1 and 2 were repeated, thereby obtaining compounds indicated in Table 7.

TABLE 7

| Compound (I) R' | R | Yield (%) | Melting Point (°C.) | IR (KBr) (cm$^{-1}$) Found | Elemental Analysis (%) Calculated Found | |
|---|---|---|---|---|---|---|
| | | | | | C | H |
| CH$_3$CO | cyclohexyl (H) | 93 | 82.0–82.5 | 1705 (C=O) 1745 (C=O) | 70.81 70.99 | 6.99 7.08 |
| CH$_3$CO | —CH(CH$_3$)$_2$ | 96 | Oil | 1700 (C=O) 1750 (C=O) Film | 67.73 67.55 | 6.50 6.24 |

What is claimed as new and desired to be secured by Letters Patent of the United States is:

1. A melanin inhibitor which comprises (1) between 0.01 to 50 wt. % of a cinnamic acid derivative of the general formula

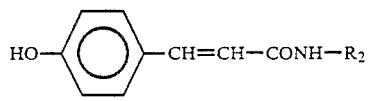

in which R$_2$ represents a hydrogen atom, an alkyl group having 1 to 24 carbon atoms, a cycloalkyl group or an alkenyl group and (b) a skin-treating base compatible with said cinnamic acid derivative.

2. The melanin inhibitor of claim 1, which further contains a humectant, thickener, preservative, emulsifier, perfume, or stabilizer.

3. The melanin inhibitor of claim 1, which further comprises a compound selected from the group consisting of allantoin, vitamin E acetate, glycyrrhizin, salicyclic acid, urea, coix seed or a plant extract.

* * * * *